United States Patent [19]
Hull

[11] Patent Number: 5,192,297
[45] Date of Patent: Mar. 9, 1993

[54] APPARATUS AND METHOD FOR PLACEMENT AND IMPLANTATION OF A STENT

[75] Inventor: Vincent W. Hull, Fridley, Minn.

[73] Assignee: Medtronic, Inc., Minneapolis, Minn.

[21] Appl. No.: 815,449

[22] Filed: Dec. 31, 1991

[51] Int. Cl.⁵ .................................................. A61F 2/06
[52] U.S. Cl. .................................. 606/195; 606/108; 604/96; 623/1
[58] Field of Search ............... 606/191, 192, 194, 195, 606/198, 108; 623/1, 12; 604/96; 128/898

[56] References Cited

U.S. PATENT DOCUMENTS

| | | | |
|---|---|---|---|
| 4,732,152 | 3/1988 | Wallsten | 623/1 |
| 4,733,665 | 3/1988 | Palmaz | 604/104 |
| 4,787,899 | 11/1988 | Lazarus | 623/1 |
| 4,878,906 | 11/1989 | Lindemann et al. | 623/1 |
| 4,886,062 | 12/1989 | Wiktor | 623/1 |
| 4,976,690 | 12/1990 | Solar et al. | 606/194 |
| 4,990,155 | 2/1991 | Wilkoff | 606/191 |
| 4,998,539 | 3/1991 | Delsanti et al. | 606/194 |
| 5,019,085 | 5/1991 | Hillstead | 606/108 |
| 5,019,090 | 5/1991 | Pinchuk | 606/194 |
| 5,090,422 | 2/1992 | Dahl et al. | 128/784 |
| 5,108,416 | 4/1992 | Ryan et al. | 623/1 |

Primary Examiner—Edgar S. Burr
Assistant Examiner—Ren Yan
Attorney, Agent, or Firm—Daniel W. Latham; Harold R. Patton

[57] ABSTRACT

A stent delivery system and method in which stent is routed to a desired position within a subject's vessel by means of a guiding catheter and dilation balloon carried by the guiding catheter proximally with respect to the stent is then moved into a position within the stent so as to expand the stent radially for implantation.

7 Claims, 3 Drawing Sheets

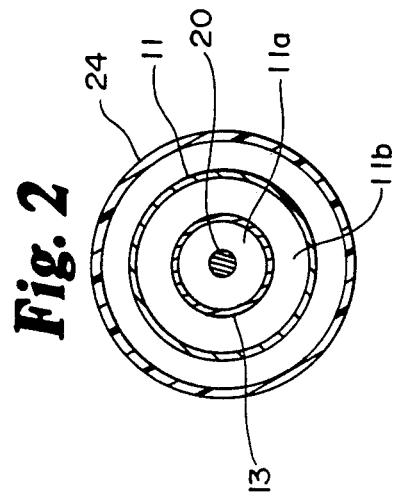
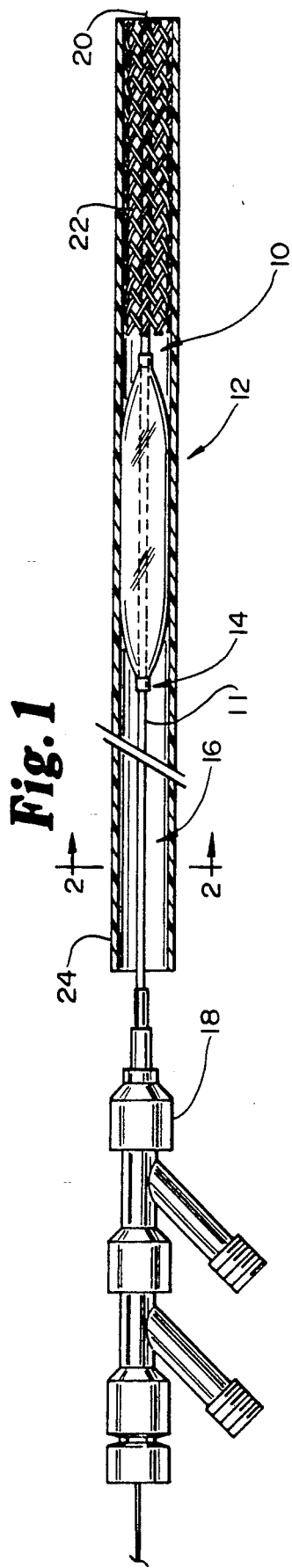

APPARATUS AND METHOD FOR PLACEMENT AND IMPLANTATION OF A STENT

BACKGROUND OF THE INVENTION

Generally, the present invention relates to a method and apparatus for positioning a stent within a body vessel, typically a blood vessel. The invention is particularly applicable to polymeric stents which though self expandable, typically have low radial strength. Due to differences in mechanical properties, self expanding, polymeric stents of a mesh design do not have the radial expansion force that metallic stents do. Because of this decreased radial force, polymeric stents seldomly completely expand against vessel walls by themselves. Complete expansion against the vessel wall is critical for proper stent implantation. The apparatus of the present invention was designed to ensure complete stent expansion. The elements of the apparatus are combined and arranged in such a way as to foster delivery, positioning, implantation and withdrawal with minimal trauma.

Stents are typically implanted within the vascular system to reinforce collapsing, partially occluded, weakened or under dilated sections of vessel. Stents have also been successfully implanted in urinary tracts and bile ducts to reinforce those body vessels. This invention is applicable in all of these situations.

In general, the typical procedure for implanting a self expanding stent is to first open the region of the vessel with a balloon catheter and then place the stent in a position bridging the weakened the portion of the vessel. Positioning of the stent may be followed by the technique known as the "Swiss Kiss" in which a separate balloon catheter is positioned within the stent and expanded to radially expand the stent for implantation.

Many patents refer to the construction and design of both stents as well as apparatus for positioning the stent within a vessel. One such patent is U.S. Pat. No. 4,140,126 to Chaudhury which issued Feb. 20, 1979. This patent disclosures a technique for positioning an elongated cylinder at a region of an aneurysm to avoid failure of the blood vessel wall. The patent discloses a cylinder that expands to its implanted configuration after insertion with the aid of a catheter.

A patent to Dotter, U.S. Pat. No. 4,503,569 which issued Mar. 12, 1985 discloses a spring stent which expands to an implanted configuration with a change in temperature. The spring stent is implanted in a coil orientation and heated to cause the spring to expand.

U.S. Pat. No. 4,733,665 to Palmaz which issued Mar. 29, 1988, discloses a number of stent configurations for implantation with the aid of a catheter. The catheter includes a mechanism for mounting and retaining the vascular prosthesis or stent, preferably on an inflatable portion of the catheter. The stent is implanted by positioning it within the blood vessel and monitoring its position on a viewing monitor. Once the stent is positioned as desired, the catheter is expanded and the stent is separated from the catheter body. The catheter can then be withdrawn from the subject, leaving the stent in place within the blood vessel.

U.S. Pat. No. 5,019,090 to Pinchuk, issued May 28, 1991, discloses delivery of a stent within a guiding catheter in combination with a dilation balloon in which the balloon is distally positioned relative to the stent.

U.S. Pat. No. 4,886,062 to Wiktor issued Dec. 12, 1989 and assigned to the same assignee as is the subject invention, discloses a stent carried on a dilation balloon which is positioned via a guiding catheter.

SUMMARY OF THE INVENTION

The present invention provides an apparatus for stent placement and implantation in which the elements of the apparatus are arranged with respect to each other for simplified and improved operation in a controlled manner.

In accordance with the invention a balloon catheter coaxially carries on the end thereof a radially expandable stent, preferably of polymeric material, the stent being distally positioned with respect to the balloon on the catheter. The catheter sheath and stent are placed in a guiding catheter in such a way that the stent may emanate from the distal end thereof for positioning in a vessel or the like followed by the balloon which is then positioned within the stent to expand it for implantation.

BRIEF DESCRIPTION OF THE DRAWINGS

FIG. 1 is a schematic depiction of a stent delivery apparatus of the invention including a balloon catheter carrying on its distal end a radially expandable stent, all of which are carried within a catheter sheath;

FIG. 2 is a schematic cross-section of the apparatus shown in FIG. 1, taken along line 2—2.

DESCRIPTION OF THE PREFERRED EMBODIMENTS

Figure 3A:
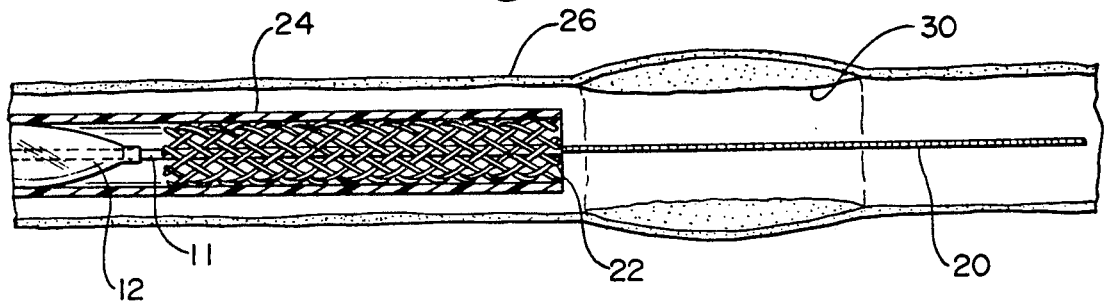
FIGS. 3a-3g are schematic diagrams showing the apparatus of the invention in use.

A preferred embodiment of the invention is shown generally in FIGS. 1 and 2. The apparatus includes a balloon catheter having a distal end area generally designated at 10 in FIG. 1, an inflatable balloon area generally designated at 12, an intermediate portion generally designated at 14 and a shaft portion generally designated at 16. Shaft portion 16 extends all the way to the proximal end of the catheter and includes an appropriate fitting or hub assembly 18 for connection to means for applying dilation pressure as is already known and practiced in the art (not shown) and for admitting a guide wire 20 which extends through the catheter and out of the tip area 10.

The construction of the balloon catheter portion of the apparatus as shown in FIG. 2 (enclosed for illustration), is typical of those known in the art in which a double hollow tube 11 is provided which runs the entire length of the catheter and which defines a central first lumen 11a and a surrounding lumen 11b. Tube 11 may be made of any number of materials, typically polyethylene. The central lumen 11a of inner tube 11 receives a guide wire 20 in use so that the catheter can be advanced over the guide wire to the site of interest. Lumen 11b is the balloon inflation lumen, arranged as is known in the art for pressurization of the balloon.

The apparatus as seen in the FIGS. 1 and 2 also comprises a hollow outer tube or catheter sheath 24 of significant inside diameter to receive the balloon catheter and also define an annular lumen between the inside diameter of sheath 24 and the balloon catheter positioned within sheath 24. Sheath 24 can be made of any suitable material and will typically also be of polyethylene or PTFE.

In accordance with this invention, a radially expandable polymeric stent of generally cylindrical overall construction shown at 22 in FIG. 1 is carried on tip 10 of the balloon catheter in a coaxial arrangement. The catheter and stent are in turn carried within catheter sheath 24. As shown in FIG. 1, tip 10 of the balloon catheter and the stent 22 are carried within catheter sheath 24 near the distal end thereof with stent 22 being more distally positioned than balloon 12.

The operation of the apparatus of the present invention is shown diagrammatically in FIG. 3a–g. Operation of the apparatus is as follows. Referring to FIG. 3a, during implantation of stent 22, catheter sheath 24 containing the apparatus shown in FIG. 1 is positioned within a vessel 26 or the like proximal to a lesion 30 which may have been pre-dilated if necessary.

Figure 3B:
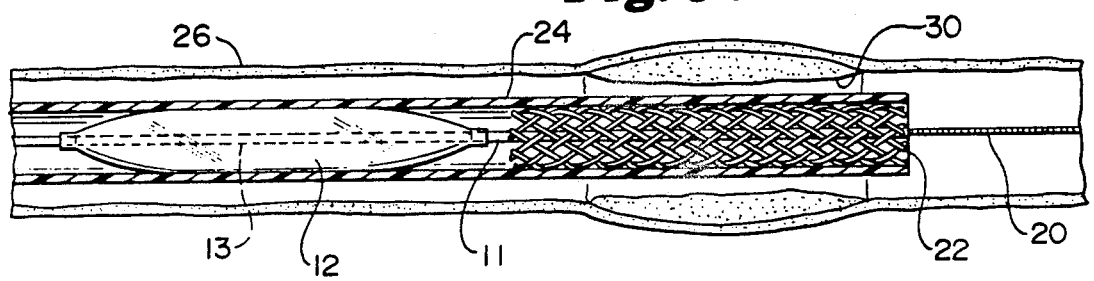

Catheter sheath 24 is then moved into the lesion 30 area so as to position stent 22 therein as shown in FIG. 3b.

Figure 3C:
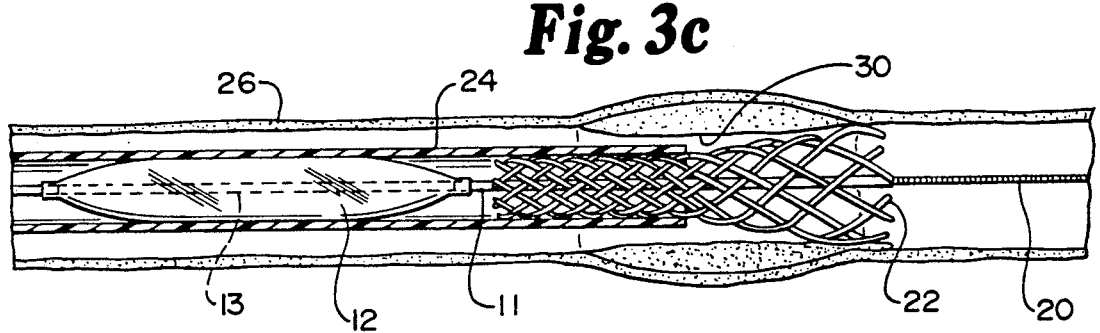

As shown in FIG. 3c the catheter sheath 24 is then withdrawn while the balloon catheter is held in place so as to cause stent 22 to be ejected from the end of catheter sheath 24 within the lesion area 30. The proximal end of stent 22 may be positioned against the distal end of balloon 12 to prevent the stent from sliding proximally.

Figure 3D:
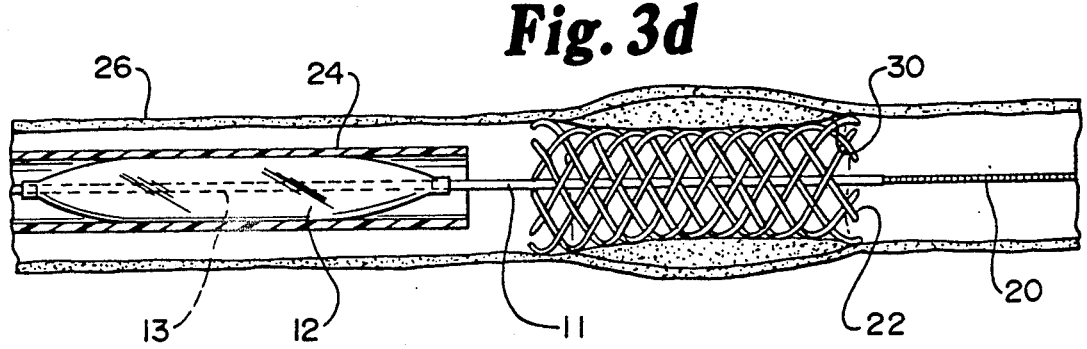

The completion of withdrawal of catheter sheath 24 from the proximal area of lesion 30 leaves stent 22 in place and partially expanded as can be seen in FIG. 3d.

Figure 3E:
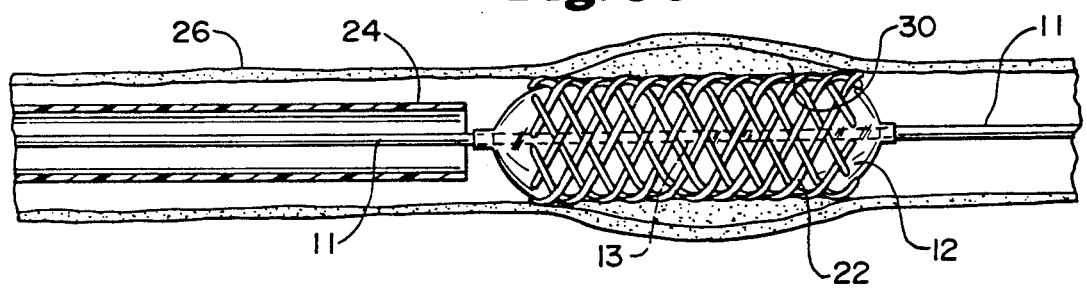
Figure 3F:
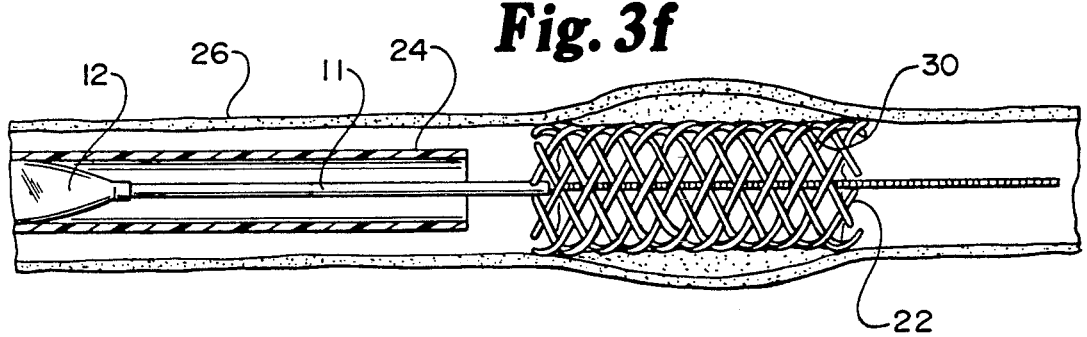

As shown in FIG. 3e balloon 12 is then advanced internally of stent 22 and expanded so as to expand stent 22 and complete its implantation into the lesion area 30. Following this as shown in FIG. 3f balloon 12 is deflated and withdrawn into catheter sheath 24, leaving stent 22 embedded in lesion 30.

Figure 3G:
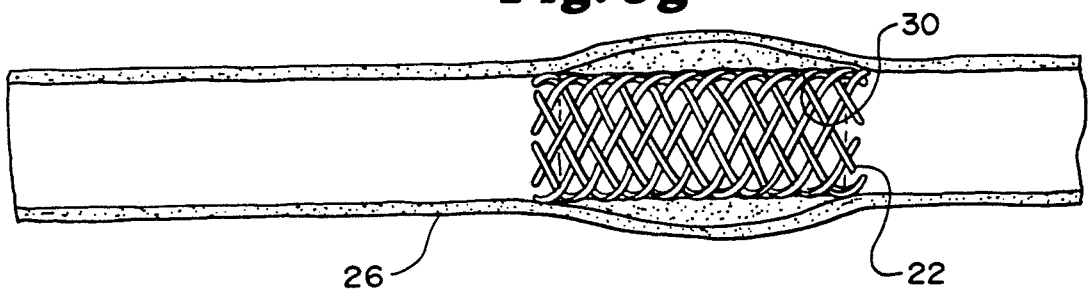

Lastly, withdrawal of the catheter sheath 24 and the balloon catheter leaves the implanted stent as shown in FIG. 3g.

This completes the description of the preferred embodiments of the invention. Those skilled in the art may recognize other equivalents to the specific embodiment described herein which equivalents are intended to be encompassed by the claims attached hereto.

What is claimed is:

1. Apparatus for placement and implantation of a stent, the apparatus comprising in combination:
   a catheter having proximal and distal ends,
   an elongate cylindrical outer sheath enclosing a distal portion of the catheter,
   a balloon on the catheter being adapted for inflation and deflation in site,
   a radially self-expandable stent of generally cylindrical configuration carried coaxially on the catheter in a distal position with respect to the balloon and enclosed within the sheath, and
   means for distally ejecting the stent from the sheath, whereby the stent may be positioned at a selected implant site by placement of the distal end of the catheter and ejected out of the sheath in a distal direction to position it at the selected site followed by insertion of the balloon coaxially in the stent and expansion thereof to implant the stent at the selected site.

2. The apparatus of claim 1 in which the stent is comprised of polymeric material.

3. The apparatus of claim 1 in which the outer sheath is comprised of polymeric material.

4. The apparatus of claim 3 in which the material is PTFE.

5. The apparatus of claim 1 wherein the sheath is open at a distal end and the stent is ejected from the open end of the sheath by longitudinal motion of the sheath relative to the stent.

6. A method of implanting a radially expandable stent, comprising the following sequence of steps:
   placing a radially self-expandable stent on a balloon catheter on the distal side of the balloon;
   positioning the catheter to place the stent proximate a selected implantation site;
   ejecting the stent from the catheter at the site;
   positioning the balloon coaxially within the ejected stent;
   inflating the balloon to implant the stent;
   deflating the balloon, and removing the balloon catheter.

7. A method of implanting a radially expandable stent comprising:
   providing a balloon catheter having a radially self-expandable stent positioned coaxially on the catheter in a distal position with respect to the balloon, the balloon and stent being enclosed within an elongate sheath member,
   positioning the stent proximate a selected implantation site,
   ejecting the stent from the sheath by moving the sheath member in a proximal direction while allowing the stent to move distally out of the sheath into position at the selected site,
   positioning the balloon within the ejected stent by moving the balloon in a distal direction out of the sheath and into co-axial relation within the stent,
   inflating the balloon to implant the stent,
   deflating the balloon and withdrawing it back in the sheath, and
   removing the sheath and catheter.

* * * * *